United States Patent
Honda et al.

(10) Patent No.: US 6,172,234 B1
(45) Date of Patent: Jan. 9, 2001

(54) OPTICALLY ACTIVE CYCLIC AMINO ACID ESTER DERIVATIVES AND PROCESSES FOR PRODUCING THE SAME

(75) Inventors: Yukihiro Honda, Ashiya; Miyuki Oikawa, Ibaraki; Isao Kurimoto, Suita, all of (JP)

(73) Assignee: Sumitomo Chemical Company, Limited, Osaka (JP)

( * ) Notice: Under 35 U.S.C. 154(b), the term of this patent shall be extended for 0 days.

(21) Appl. No.: 09/361,222

(22) Filed: Jul. 27, 1999

(30) Foreign Application Priority Data

Jul. 27, 1998 (JP) .................................. 10-210874

(51) Int. Cl.[7] ........................ C07D 211/60; C07D 207/00
(52) U.S. Cl. ........................................ 546/227; 548/532
(58) Field of Search .............................. 548/532; 546/227

(56) References Cited

U.S. PATENT DOCUMENTS

| | | | |
|---|---|---|---|
| 2,794,025 | * 5/1957 | Amiard et al. | 548/532 |
| 3,976,660 | * 8/1976 | Ondetti et al. | 548/532 |
| 4,310,461 | * 1/1982 | Krapcho et al. | 546/227 |
| 4,937,355 | * 6/1990 | Kloss et al. | 548/532 |
| 5,753,679 | * 5/1998 | Riemer | 546/227 |
| 5,880,291 | 3/1999 | Ushio et al. | 548/953 |
| 5,929,243 | * 7/1999 | Askin et al. | 546/227 |

FOREIGN PATENT DOCUMENTS

| | | |
|---|---|---|
| 0 827 954 | 3/1998 | (EP) . |
| 2-229152 | 9/1990 | (JP) . |

OTHER PUBLICATIONS

Sheradsky et al, "Intramolecular nucleophilic substitution on nitrogen", CA124:56616 of Tet. Lett., 36(42), 7701–4, 1995.*

Kawaguchi et al, "An asymmetric synthesis of 2–substituted piperidines . . . ", CA108:167736 of Agric. Biol. Chem. 50(12), 3107–12, 1986.*

Koh–ichi Aketa et al., "Stereochemical Studies. XL.[1]) A Biomimetic Conversion of L–Lysine into optically Active 2–Substituted Piperidines. Synthesis of D– and L–Pipecolic Acid, and (S) (+)–Coniine from L–Lysine[2])", *Chem. Pharm. Bull.*, vol. 24, No. 4, 1976, pp. 621–631.

L. Baláspiri et al, "Die Herstellung von für die Peptidsynthese geeigneten, optisch aktiven Pipecolinsäurederivaten", *Monatshefte für Chemie,*vol. 101, 1970, pp. 1177–1183, English Abstract of German Patent Application No. DE 2440212, 1976.

Tadashi Shiraiwa et al., "Asymmetric Transformations of Proline and 2–Piperidinecarboxylic Acid via Formation of Salts with Optically Actie Tartaric Acid", *Bull. Chem. Soc. Jpn.*, vol. 64, 1991, pp. 3251–3255.

Robert T. Shuman et al., "An Improved Synthesis of Homoproline and Derivatives", *J. Org. Chem.*, vol. 55, 1990, pp. 738–741.

Wim A. J. Starmans et al., "Azetidine based Ligands in Boron catalyzed Asymmetric Diels–Alder Reactions", *Tetrahedron*, vol. 54, 1998, pp. 4991–5004, May.

Serge Nazabadioko, et al., "Chemoenzymatic synthesis of (S)–2–cyanopiperidine, a key intermediate in the route to (S)–pipecolic acid and 2–substituted piperidine alkaloids", *Tetrahedron: Asymmetry*, vol. 9, 1998, pp. 1597–1604.

\* cited by examiner

*Primary Examiner*—Deborah C. Lambkin
(74) *Attorney, Agent, or Firm*—Sughrue, Mion, Zinn, Macpeak & Seas, PLLC

(57) ABSTRACT

There are disclosed a process for producing the optically active cyclic amino acid ester derivative of the formula (I):

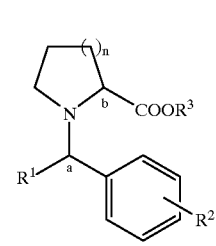

(I)

by optical resolution method, a process for producing the same and a process for producing an optically active cyclic amino acid using the compound of the formula (I).

16 Claims, No Drawings

OPTICALLY ACTIVE CYCLIC AMINO ACID ESTER DERIVATIVES AND PROCESSES FOR PRODUCING THE SAME

BACKGROUND OF THE INVENTION

1. Field of the Invention

The present invention relates to novel useful intermediates for producing optically active cyclic amino acids (for example, optically active proline, pipecolic acid, etc.), which are useful for producing pharmaceuticals, agrochemicals and the like, and to processes for producing and using the same.

2. Description of Related Art

Heretofore, a process has been known as processes for producing racemic proline and pipecolic acid, in which process pyrrolecarboxylic acid or pyridinecarboxylic acid is hydrogenated [Journal of Organic Chemistry, 1990, 55, 738].

Although processes in which racemic proline or pipecolic acid is optically resolved with tartaric acid have been known [Bulletin Chemical Society of Japan, 64, 3251 (1991)], such processes have a problem in separation of proline or pipecolic acid from the resolving agents.

Processes also have been known in which proline or pipecolic acid is first converted into N-(benzyloxycarbonyl) proline or N-(benzyloxycarbonyl)pipecolic acid, which is then subjected to optical resolution with optically active tyrosine hydrazide, and then a hydrogenolysis [Monatshefte fur Chemie 101, 1177 (1970)], but such processes have drawbacks in that they require expensive and not readily available resolving agent in an industrial scale.

As a process for producing optically active pipecolic acid, a process also has been known in which process optically active lysine is used [Chem. Pharm. Bull., 24, 621 (1976), Japanese unexamined patent publication No. Hei 2-229152], but it is not always satisfactory in an optical purity.

SUMMARY OF THE INVENTION

An object of the invention is to provide a novel process for producing an optically active cyclic amino acid ester compound, which can be further derivatized to the optically active cyclic amino acids, by using readily available inexpensive di-substituted aliphatic carboxylic acids and resolving agents.

It is also an object of the invention to provide the novel optically active cyclic amino acid and its derivatives.

A further object of the invention is to provide processes for producing the optical active cyclic amino acids from the novel derivatives.

The present invention provides:

1. A process for producing the optically active cyclic amino acid ester derivative of the formula (I):

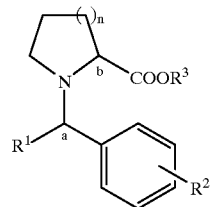

wherein $R^1$ represents a C1–C8 alkyl group;
$R^2$ represents a hydrogen atom, a C1–C8 alkyl group, a halogen atom, a hydroxy group or a C1–C8 alkoxy group;
$R^3$ represents an aryl group or a C1–C8 alkyl group, which alkyl group may be substituted with an aryl group;
"n" represents an integer from 1 to 4; and
"a" and "b" independently represent R or S,
which comprises the steps of:
(a) contacting a cyclic amino acid ester derivative of the formula (II):

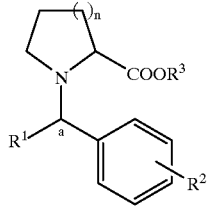

wherein $R^1$, $R^2$, $R^3$, "n" and "a" represent the same as defined above, with an optically active carboxylic acid of the formula (III):

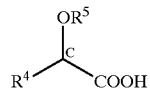

wherein $R^4$ represents:
a C1–C8 linear or branched alkyl group which may be substituted with at least one group selected from a phenyl group, a hydroxy group, a C1–C8 alkoxy group, a phenoxy group, an acyloxy group (e.g., C1–C8 alkanoyloxy and C7–C11 arylcarbonyloxy) a hydroxycarbonyl group, an C1–C8 alkoxycarbonyl group and a halogen atom;
a phenyl group which may be substituted with at least one group selected from a C1–C8 alkyl group, a phenyl group, a hydroxy group, a C1–C8 alkoxy group, a phenoxy group, an acyloxy group (e.g., C1–C8 alkanoyloxy and C7–C11 arylcarbonyloxy) and a halogen atom; or a halogen atom;
$R^5$ represents:
a C1–C8 linear or branched alkyl group which may be substituted with at least one group selected from a phenyl group, a hydroxy group, a C1–C8 alkoxy group, a phenoxy group, an acyloxy group (e.g., C1–C8 alkanoyloxy and C7–C11 arylcarbonyloxy) and a halogen atom;

a phenyl group which may be substituted with at least one group selected from a C1–C8 alkyl group, a phenyl group, a hydroxy group, a C1–C8 alkoxy group, a phenoxy group, an acyloxy group (e.g., C1–C8 alkanoyloxy and C7–C11 arylcarbonyloxy), a halogen atom and a nitro group;

an acyl group (e.g., C1–C8 alkanoyl and C7–C11 arylcarbonyl) which may be substituted with at least one group selected from a C1–C8 alkyl group, a phenyl group, a hydroxy group, a C1–C8 alkoxy group, a phenoxy group, an acyloxy group (e.g., C1–C8 alkanoyloxy and C7–C11 arylcarbonyloxy), a halogen atom and a nitro group; or a hydrogen atom;

"c" represents R or S;

(b) isolating a resulting salt comprising the compounds of the formulae (I) and (III); and (c) treating the isolated salt with an acid or a base.

2. An optically active cyclic amino acid ester derivative of the formula (I) as described above;

3. A salt comprising the optically active cyclic amino acid ester derivative of the formula (I) as defined above and an optically active carboxylic acid of the formula (III) as defined above;

4. An optically active cyclic amino acid derivative of the formula (IV):

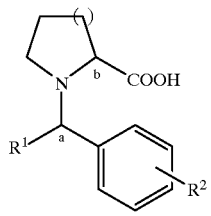

(IV)

wherein $R^1$, $R^2$, "n", "a" and "b" respectively have the same meaning as defined above;

5. A process for producing the optically active cyclic amino acid derivative of the formula (IV) as defined above, which comprises:
hydrolyzing the optically active cyclic amino acid ester derivative of the formula (I) as defined above in the presence of an acid or a base.

6. A process for producing an optically active cyclic amino acid of the formula (V):

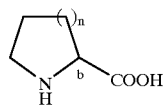

(V)

wherein "n" is an integer of 1 to 4, and "b" represents R or S, which comprises:

subjecting the optically active cyclic amino acid derivative of the formula (IV) as defined above to a hydrogenolysis reaction in the presence of a catalyst;

7. A cyclic amino acid ester derivative of the formula (II):

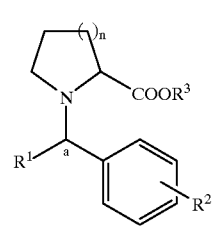

(II)

wherein $R^1$, $R^2$, $R^3$ and "a" represent the same as defined above, and "n" represents an integer from 2 to 4;

8. A process for producing an optically active cyclic amino acid ester derivative of the formula (I) as defined above, which comprises:
reacting a di-substituted aliphatic carboxylic acid ester of the formula (VI):

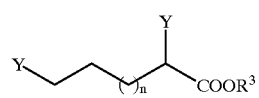

(VI)

wherein Y represents a leaving group,
$R^3$ and "n" have the same meaning defined above,
with an optically active amine of the formula (VII):

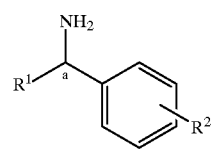

(VII)

wherein $R^1$, $R^2$ and "a" have the same meaning defined above.

DETAILED DESCRIPTION OF THE INVENTION

In the present invention, the C1–C8 alkyl group in the formula (I) through (VII) includes a methyl group, an ethyl group, an isopropyl group, a butyl group, a pentyl group, a hexyl group, a heptyl group and an octyl group.

The C1–C8 alkoxyl group includes a methoxy group, an ethoxy group, an n-propoxy group, an i-propoxy group, a butoxy group, a pentyloxy group, a hexyloxy group, a heptyloxy group and an octyloxyl group.

The halogen atom includes a fluorine atom, a chlorine atom, a bromine atom and an iodine atom.

Examples of the aryl group for $R^3$ include a C6–C10 aryl group such as a phenyl group, a tolyl group and a naphthyl group.

Examples of the C1–C8 alkyl group which may be substituted with an aryl group for $R^3$ include a C1–C8 alkyl group which may be substituted a phenyl group or a tolyl group.

In the chemical formula of the present invention, "a", "b" and "c" mean either R or S configuration around the carbon atom to which the notations are attached.

Next, a description will be made to the process for producing the optically active cyclic amino acid ester derivative of the formula (I) as defined above,
which comprises the steps of:
(a) contacting a diastereomeric mixture of cyclic amino acid ester derivative of the formula (II) as defined above with an optically active carboxylic acid of the formula (III) as defined above
(b) isolating a resulting salt comprising the compounds of the formulae (I) and (III); and
(c) treating the isolated salt with an acid or a base.

Specific examples of such an optically active cyclic amino acid ester derivative of the formula (I) include N-[(S)-α-methylbenzyl]-(S)-proline methyl ester, N-[(S)-α-methylbenzyl]-(R)-proline methyl ester, N-[(R)-α-methylbenzyl]-(S)-proline methyl ester, N-[(R)-α-methylbenzyl]-(R)-proline methyl ester, methyl N-[(S)-α-methylbenzyl]-(S)-pipecolate, methyl N-[(S)-α-methylbenzyl]-(R)-pipecolate, methyl N-[(R)-α-methylbenzyl]-(S)-pipecolate, methyl N-[(R)-α-methylbenzyl]-(R)-pipecolate, and compounds having ethyl, butyl, octyl, isopropyl, benzyl, methylbenzyl, phenethyl or phenyl in place of the methyl group as the alkyl residue of the ester compounds above.

The cyclic amino acid ester derivative of the formula (II) or a salt thereof represents a diastereomeric mixture containing an optical isomer of the formula (I) and a diastereomer thereof. The cyclic amino acid ester derivatives may be salts thereof such as hydrochloride salt and phosphate salt.

Specific examples of such a diastereomeric mixture include a mixture of N-[(S)-α-methylbenzyl]-(S)-proline methyl ester and N-[(S)-α-methylbenzyl]-(R)-proline methyl ester, a mixture of N-[(R)-α-methylbenzyl]-(S)-proline ethyl ester and N-[(R)-α-methylbenzyl]-(R)-proline ethyl ester or salts thereof.

In the optically active carboxylic acid of the formula (III), examples of the $R^4$ in the optically active carboxylic acid of the formula (III) include a phenyl group, a methyl group, an ethyl group, a hydroxycarbonylmethyl group, a 1-(hydroxy) hydroxycarbonylmethyl group, a 1-(benzoyloxy) hydroxycarbonylmethyl group, etc.

Specific examples of the $R^5$ include a hydrogen atom, a methyl group, an ethyl group, a benzoyl group, etc.

Specific examples of the optically active carboxylic acid of the formula (III) include L-mandelic acid, D-mandelic acid, L-malic acid, D-malic acid, L-tartaric acid, D-tartaric acid, L-O,O'-dibenzoyltartaric acid and D-O,O'-dibenzoyltartaric acid.

The amount of the optically active carboxylic acid used is usually 0.1 to 10 moles, preferably 0.3 to 2 moles, per mole of the cyclic amino acid ester derivative (II).

The reaction of step (a) can be usually carried out in the presence of a solvent. The solvent is not particularly limited unless it inhibits the reaction, and may be water, alcohol solvents such as methanol, ethanol and 2-propanol, nitrile solvents such as acetonitrile, hydrocarbon solvents such as toluene, benzene, xylene, hexane and heptane, halogenated hydrocarbon solvents such as dichloromethane, dichloroethane, chloroform, chlorobenzene and orthodichlorobenzene, ether solvents such as diethyl ether and tert-butyl methyl ether, amide solvents such as acetamide, N,N-dimethylformamide and N,N-dimethylacetamide, nitro solvents such as nitrobenzene and nitromethane, and sulfoxide solvents such as dimethyl sulfoxide, etc. These solvents may be used either alone or as a mixture of two or more of them. The amount of the solvent used is usually 0.01 to 100 parts by weight, preferably 0.01 to 20 parts by weight, per part by weight of the cyclic amino acid ester derivative.

The reaction is carried out, for example, by mixing the diastereomeric mixture of the optically active cyclic amino acid ester derivatives and the optically active carboxylic acid. In the case where the solvent is used, the cyclic amino acid ester derivative and the optically active carboxylic acid may be mixed in the solvent. The reaction temperature is usually −80° C. to 200° C., preferably −20° C. to 100° C.

Through such a reaction, a salt of one of the optically active cyclic amino acid ester derivatives and the resulting optically active salts preferentially forms and precipitates. After the reaction, the optically active substance can be easily separated by a conventional method such as filtration. The product may be further purified by recrystallization and the like.

The other diastereomeric salt, which is contained in the filtrate can be readily isolated by, for example, evaporation of the solvent from the filtrate.

The optically active cyclic amino acid ester derivative of the formula (I) can be readily obtained by a treatment of the salt comprising the optically active cyclic amino acid ester derivative (I) and the optically active carboxylic acid (III) with an acid or a base.

Example of the acid used in the acid treatment include inorganic acids such as hydrochloric acid, sulfuric acid and phosphoric acid, and organic acids such as methanesulfonic acid, p-toluenesulfonic acid and trifluoroacetic acid. These acids may be used either alone or as a mixture of two or more of them. The amount thereof is usually 0.5 to 10 moles, preferably 1 to 2 moles, per mole of the salt of the optically active cyclic amino acid ester derivative (I) and the optically active carboxylic acid (III).

Examples of the base used in the base treatment include alkali metal hydroxides such as lithium hydroxide, sodium hydroxide and potassium hydroxide, alkaline earth metal hydroxides such as calcium hydroxide, alkali metal carbonates such as sodium carbonate and potassium carbonate, alkali metal hydrogencarbonates such as sodium hydrogencarbonate and potassium hydrogencarbonate, alkaline earth metal hydrogencarbonates such as calcium hydrogencarbonate, phosphates such as disodium hydrogenphosphate, and dipotassium hydrogenphosphate, and organic bases such as triethylamine and tributylamine. These bases may be used either alone or a mixture of two or more of them. The amount thereof is usually 0.5 to 10 moles, preferably 1 to 2 moles, per mole of the salt of the optically active cyclic amino acid ester derivative and the optically active carboxylic acid.

The reaction can be usually carried out in the presence of a solvent. The solvent is not particularly limited unless it adversely affect the reaction, and may be water, alcohol solvents such as methanol, ethanol and 2-propanol, nitrile solvents such as acetonitrile, hydrocarbon solvents such as toluene, benzene, xylene, hexane and heptane, halogenated hydrocarbon solvents such as dichloromethane, dichloroethane, chloroform, chlorobenzene and o-dichlorobenzene, ether solvents such as diethyl ether and tert-butyl methyl ether, amide solvents such as acetamide, N,N-dimethylformamide and N,N-dimethylacetamide, nitro solvents such as nitrobenzene and nitromethane, and sulfoxide solvents such as dimethyl sulfoxide, etc. These solvents may be used either alone or as a mixture of two or more of them. The amount of the solvent used is usually 0.01 to 100 parts by weight, preferably 0.01 to 20 parts by weight, per part by weight of the salt of the optically active cyclic amino acid ester derivative and the optically active carboxylic acid.

The reaction is carried out, for example, by mixing the salt of the optically active cyclic amino acid ester derivative (I) and the optically active carboxylic acid (III) with an acid or a base. In the case where the solvent is used, the salt of the cyclic amino acid ester derivative (I) and the optically active carboxylic acid (III) may be mixed with the acid or the base in the solvent. The reaction temperature is usually −80° C. to 200° C., preferably −20° C. to 100° C.

The optically active cyclic amino acid derivative of the formula (IV) can be easily prepared by hydrolyzing the foregoing optically active cyclic amino acid ester derivative in the presence of an acid or a base.

Specific examples of the optically active cyclic amino acid derivative (IV) include N-[(S)-α-methylbenzyl]-(S)-proline, N-[(S)-α-methylbenzyl]-(R)-proline, N-[(R)-α-methylbenzyl]-(S)-proline, N-[(R)-α-methylbenzyl]-(R)-proline, N-[(S)-α-methylbenzyl]-(S)-pipecolic acid, N-[(S)-α-methylbenzyl]-(R)-pipecolic acid, N-[(R)-α-methylbenzyl]-(S)-pipecolic acid, N-[(R)-α-methylbenzyl]-(R)-pipecolic acid. In addition, these optically active cyclic amino acid derivatives and the diastereomer mixtures thereof may be either salts formed with an acid, such as hydrochloride and phosphate or salts formed with a base, such as a sodium salt, a potassium salt and an ammonium salts.

Example of the acid used in the hydrolysis reaction include inorganic acids such as hydrochloric acid, sulfuric acid and phosphoric acid, and organic acids such as methanesulfonic acid, p-toluenesulfonic acid, acetic acid, trifluoroacetic acid and 2-ethylhexanoic acid.

Examples of the base include alkali metal hydroxides such as sodium hydroxide and potassium hydroxide, alkaline earth metal hydroxides such as barium hydroxide and calcium hydroxide, alkali metal carbonates such as sodium carbonate and potassium carbonate, alkali metal hydrogencarbonates such as sodium hydrogencarbonate and potassium hydrogencarbonate, and alkoxides such as sodium methoxide and potassium tert-butoxide.

The amount of the acid or the base used is usually 0.1 to 20 moles, preferably 0.1 to 5 moles, per mole of the optically active cyclic amino acid ester derivative. The amount of water used is usually 1 to 100 parts by weight per part by weight of the optically active cyclic amino acid ester derivative.

The reaction is carried out, for example, by mixing the optically active cyclic amino acid ester derivative (I) and the acid or the base in water. The reaction temperature is usually −50° C. to 200° C., preferably −20° C. to 150° C.

The reaction may take place in the presence of an organic solvent. The organic solvent is not particularly limited unless it inhibits the reaction, and may be alcohol solvents such as methanol, ethanol and 2-propanol, nitrile solvents such as acetonitrile, hydrocarbon solvents such as toluene, benzene, xylene, hexane and heptane, halogenated hydrocarbon solvents such as dichloromethane, dichloroethane, chloroform, chlorobenzene and orthodichlorobenzene, ether solvents such as diethyl ether and tert-butyl methyl ether, amide solvents such as acetamide, N,N-dimethylformamide and N,N-dimethylacetamide, nitro solvents such as nitrobenzene and nitromethane, and sulfoxide solvents such as dimethyl sulfoxide, etc.

The optically active cyclic amino acid derivative (IV) can be obtained from the reaction mixture after the reaction by a conventional method such as evaporation of the solvent. The optically active cyclic amino acid derivative (IV) can be obtained in the form of salt with the acid or the base used in the previous reaction. The acid or base, which can form an insoluble salt by neutralization, can be previously removed by a method in which the salt formed through neutralization is separated by filtration, and the optically active cyclic amino acid derivative (IV) can be obtained in a betaine form.

The optically active cyclic amino acid derivative of the present invention can be readily converted into the optically active cyclic amino acid of the formula (V) in a good yield by subjected to a hydrogenolysis reaction in the presence of a catalyst.

The catalyst, examples thereof including palladium carbon, palladium hydroxide on carbon, palladium acetate, palladium chloride, palladium oxide and palladium hydroxide, is employed usually in amounts of 0.0001 to 0.5 part by weight per part by weight of the optically active cyclic amino acid derivative.

The hydrogenolysis reaction is usually carried out by using a hydrogen source such as hydrogen, hydrazine and salts thereof, e.g., its hydrochlorate and carbonate, formic acid and salts thereof, e.g., its ammonium salt.

In the reaction, a solvent is usually used, and examples thereof including water, alcohol solvents such as methanol, ethanol and 2-propanol, ester solvents such as ethyl acetate, methyl acetate and butyl acetate, nitrile solvents such as acetonitrile, aromatic hydrocarbon solvents such as toluene, xylene, ethylbenzene and benzene, aliphatic hydrocarbon solvents such as hexane and heptane, halogenated hydrocarbon solvents such as dichloromethane, dichloroethane, chloroform, chlorobenzene and orthodichlorobenzene, ether solvents such as diethyl ether and tert-butyl methyl ether, and amide solvents such as acetamide, N,N-dimethylformamide and N,N-dimethylacetamide. These solvents may be used either alone or as a mixture of two or more of them. The amount of the solvent used is usually 2 to 100 parts by weight per part by weight of the optically active cyclic amino acid derivative.

In the case where hydrogen is employed, the hydrogenolysis reaction is carried out by, for example, adding the cyclic amino acid derivative and a catalyst to a solvent, and then introducing a hydrogen gas into the reaction mixture. Feeding of the hydrogen gas may be carried out either by bubbling the hydrogen gas into the reaction mixture or by stirring the reaction system in an atmosphere of a hydrogen gas of normal or elevated pressure.

In the case where the hydrogenolysis reaction takes place in the presence of a hydrogen source, the hydrogenolysis reaction may be carried out by, for example, adding the optically active cyclic amino acid derivative and a catalyst to a solvent, and then adding a reducing agent.

The reaction temperature is −50° C. to 200° C. for the both cases.

The optically active cyclic amino acid (V) can be obtained from the reaction mixture after the reaction by a conventional method such as, for example, separating the catalyst by filtration and then evaporating the solvent from the filtrate. The product may be further purified by recrystallization, column chromatography and the like.

The process for producing the optically active cyclic amino acid ester derivative of the formula (II), which comprises reacting the di-substituted aliphatic carboxylic acid ester of the formula (VI) with the optically active amine of the formula (VII) is described below.

The di-substituted aliphatic carboxylic acid ester of the formula (VI) can be prepared by a known method. In the case of preparing methyl 2,6-dibromocaproate, it can be synthesized by a conventional reaction of ε-caprolactone with bromine in the presence of red phosphorus or phosphorus tribromide, and then esterification of the product with methanol.

In the di-substituted aliphatic carboxylic acid ester of the formula (VI), the leaving group represented by Y may be a halogen atom such as a chlorine atom a bromine atom, an iodine atom, a mesyloxy group, a tosyloxy group, a benzenesulfonyloxy group, a nitrobenzenesulfonyloxy group, etc.

Specific examples of the di-substituted aliphatic carboxylic acid ester include di-halogen-substituted valeric acid esters such as methyl 2,5-dichlorovalerate, ethyl 2,5-dichlorovalerate, butyl 2,5-dichlorovalerate, octyl 2,5-dichlorovalerate, isopropyl 2,5-dichlorovalerate, benzyl 2,5-dichlorovalerate, phenethyl 2,5-dichlorovalerate, phenyl 2,5-dichlorovalerate, methyl 2,5-dibromovalerate, ethyl 2,5-dibromovalerate, butyl 2,5-dibromovalerate, octyl 2,5-dibromovalerate, isopropyl 2,5-dibromovalerate, benzyl 2,5-dibromovalerate, phenethyl 2,5-dibromovalerate, phenyl 2,5-dibromovalerate, methyl 2,5-diiodovalerate, ethyl 2,5-diiodovalerate, butyl 2,5-diiodovalerate, octyl 2,5-diiodovalerate, isopropyl 2,5-diiodovalerate, benzyl 2,5-diiodovalerate, phenethyl 2,5-diiodovalerate and phenyl 2,5-diiodovalerate, methyl 2,5-dimesyloxyvalerate, ethyl 2,5-dimesyloxyvalerate, butyl 2,5-dimesyloxyvalerate, octyl 2,5-dimesyloxyvalerate, isopropyl 2,5-dimesyloxyvalerate, benzyl 2,5-dimesyloxyvalerate, phenethyl 2,5-dimesyloxyvalerate, phenyl 2,5-dimesyloxyvalerate, methyl 2,5-ditosyloxyvalerate, ethyl 2,5-ditosyloxyvalerate, butyl 2,5-ditosyloxyvalerate, octyl 2,5-ditosyloxyvalerate, isopropyl 2,5-ditosyloxyvalerate, benzyl 2,5-ditosyloxyvalerate, phenethyl 2,5-ditosyloxyvalerate, phenyl 2,5-ditosyloxyvalerate, methyl 2,5-dibenzenesulfonyloxyvalerate, ethyl 2,5-dibenzenesulfonyloxyvalerate, butyl 2,5-dibenzenesulfonyloxyvalerate, octyl 2,5-dibenzenesulfonyloxyvalerate, isopropyl 2,5-dibenzenesulfonyloxyvalerate, benzyl 2,5-dibenzenesulfonyloxyvalerate, phenethyl 2,5-dibenzenesulfonyloxyvalerate, phenyl 2,5-dibenzenesulfonyloxyvalerate, methyl 2,5-di(nitrobenzenesulfonyloxy)valerate, ethyl 2,5-di(nitrobenzenesulfonyloxy)valerate, butyl 2,5-di(nitrobenzenesulfonyloxy)valerate, octyl 2,5-di(nitrobenzenesulfonyloxy)valerate, octyl 2,5-di(nitrobenzenesulfonyloxy)valerate, isopropyl 2,5-di(nitrobenzenesulfonyloxy)valerate, benzyl 2,5-di(nitrobenzenesulfonyloxy)valerate, phenethyl 2,5-di(nitrobenzenesulfonyloxy)valerate, phenyl 2,5-di(nitrobenzenesulfonyloxy)valerate, di-halogen-substituted caproic acid esters such as methyl 2,6-dichlorocaproate, ethyl 2,6-dichlorocaproate, butyl 2,6-dichlorocaproate, octyl 2,6-dichlorocaproate, isopropyl 2,6-dichlorocaproate, benzyl 2,6-dichlorocaproate, phenethyl 2,6-dichlorocaproate, phenyl 2,6-dichlorocaproate, methyl 2,6-dibromocaproate, ethyl 2,6-dibromocaproate, butyl 2,6-dibromocaproate, octyl 2,6-dibromocaproate, isopropyl 2,6-dibromocaproate, benzyl 2,6-dibromocaproate, phenethyl 2,6-dibromocaproate, phenyl 2,6-dibromocaproate, methyl 2,6-diiodocaproate, ethyl 2,6-diiodocaproate, butyl 2,6-diiodocaproate, octyl 2,6-diiodocaproate, isopropyl 2,6-diiodocaproate, benzyl 2,6-diiodocaproate, phenethyl 2,6-diiodocaproate and phenyl 2,6-diiodocaproate, methyl 2,6-dimesyloxycaproate, ethyl 2,6-dimesyloxycaproate, butyl 2,6-dimesyloxycaproate, octyl 2,6-dimesyloxycaproate, isopropyl 2,6-dimesyloxycaproate, benzyl 2,6-dimesyloxycaproate, phenethyl 2,6-dimesyloxycaproate, phenyl 2,6-dimesyloxycaproate, methyl 2,6-ditosyloxycaproate, ethyl 2,6-ditosyloxycaproate, butyl 2,6-ditosyloxycaproate, octyl 2,6-ditosyloxycaproate, isopropyl 2,6-ditosyloxycaproate, benzyl 2,6-ditosyloxycaproate, phenethyl 2,6-ditosyloxycaproate, phenyl 2,6-ditosyloxycaproate, methyl 2,6-dibenzenesulfonyloxycaproate, ethyl 2,6-dibenzenesulfonyloxycaproate, butyl 2,6-dibenzenesulfonyloxycaproate, octyl 2,6-dibenzenesulfonyloxycaproate, isopropyl 2,6-dibenzenesulfonyloxycaproate, benzyl 2,6-dibenzenesulfonyloxycaproate, phenethyl 2,6-dibenzenesulfonyloxycaproate, phenyl 2,6-dibenzenesulfonyloxycaproate, methyl 2,6-di(nitrobenzenesulfonyloxy)caproate, ethyl 2,6-di(nitrobenzenesulfonyloxy)caproate, butyl 2,6-di(nitrobenzenesulfonyloxy)caproate, octyl 2,6-di(nitrobenzenesulfonyloxy)caproate, isopropyl 2,6-di(nitrobenzenesulfonyloxy)caproate, benzyl 2,6-di(nitrobenzenesulfonyloxy)caproate, phenethyl 2,6-di(nitrobenzenesulfonyloxy)caproate and phenyl 2,6-di(nitrobenzenesulfonyloxy)caproate.

Examples of the optically active amine of the formula (VII) include (S)-α-1-methylbenzylamine, (R)-α-methylbenzylamine, (S)-1-phenylpropylamine, (R)-1-phenylpropylamine, (S)-1-(p-chlorophenyl)ethylamine, (R)-1-(p-chlorophenyl)ethylamine, (S)-1-(p-bromophenyl)ethylamine, (R)-1-(p-bromophenyl)ethylamine, (S)-1-(p-tolyl)ethylamine, (R)-1-(p-tolyl)ethylamine, (S)-1-(p-methoxyphenyl)ethylamine, (R)-1-(p-methoxyphenyl)ethylamine, which may be optionally chosen depending upon the desired optically active cyclic amino acid ester derivative. The amount of such an optically active amine to be used is usually 0.5 to 20 moles, preferably 1 to 5 moles, per mole of the di-substituted aliphatic carboxylic acid ester.

The reaction between the di-substituted aliphatic carboxylic acid ester of the formula (VI) and the optically active amine of the formula (VII) may be carried out in the presence of a base.

Examples of the base include inorganic salts such as alkali metal hydroxides, e.g., sodium hydroxide and potassium hydroxide, alkaline earth metal hydroxides, e.g., barium hydroxide and calcium hydroxide, alkali metal carbonates, e.g., sodium carbonate and potassium carbonate and alkali metal hydrogencarbonates, e.g. sodium hydrogencarbonate and potassium hydrogencarbonate, and organic bases such as triethylamine and pyridine. In the case where such a base is used, it is used usually in amounts of 0.5 to 20 moles, preferably 1 to 5 moles, per mole of the di-substituted aliphatic carboxylic acid ester.

The reaction can be usually carried out in a solvent. Examples of the solvent include water, alcohol solvents such as methanol, ethanol and 2-propanol, nitrile solvents such as acetonitrile, hydrocarbon solvents such as toluene, benzene, xylene, hexane and heptane, halogenated hydrocarbon solvents such as dichloromethane, dichloroethane, chloroform, chlorobenzene and o-dichlorobenzene, ether solvents such as diethyl ether and tert-butyl methyl ether, amide solvents such as acetamide, N,N-dimethylformamide and N,N-dimethylacetamide, nitro solvents such as nitrobenzene and nitromethane, and sulfoxide solvents such as dimethyl sulfoxide. These solvents may be used alone or in combination of two or more of them. The amount thereof is usually 1 to 100 parts by weight, preferably 1 to 20 parts by weight, per part by weight of the di-substituted aliphatic carboxylic acid ester.

The reaction is, for example, carried out by mixing the di-substituted aliphatic carboxylic acid ester and the optically active amine in the solvent. In the case where the base is used, the di-substituted aliphatic carboxylic acid ester, the optically active amine and the base may be mixed in the solvent. The reaction temperature is usually −50° C. to 200° C., preferably −20° C. to 100° C.

Through such a reaction is obtained a diastereomeric mixture of optically active cyclic amino acid ester derivatives.

Separation of the diastereomeric mixture of amino acid ester (I) formed from the reaction mixture may be carried out, for example, by subjecting the reaction mixture to an extraction with a hydrophobic solvent, and then concentrating the organic layer obtained.

The optically active cyclic amino acid ester derivative (II) of the present invention can be readily prepared in a good yield by using a di-substituted aliphatic carboxylic acid ester and an optically active amine as starting materials, and can be readily converted into an optically active cyclic amino acid which is useful as an intermediate of pharmaceuticals.

EXAMPLES

The examples which follow serve to illustrate the present invention in detail without restricting it thereto.

Example 1

Methyl (RS)-2,5-dibromovalerate (24.5 g) and toluene (19.8 g) were added to a 49% aqueous potassium carbonate solution (53.3 g), and heated to 80° C. (S)-α-methylbenzylamine (12.0 g) was added dropwise to the mixture obtained above at that temperature, and was stirred at that temperature for 9.5 hours. Water (33.9 g) was added to the reaction mixture, and then the organic layer was separated from the resulting mixture. Separated organic layer was washed with water, a 1% aqueous hydrochloric acid solution and water in this order, and concentrated under reduced pressure. Thus, N-[(S)-α-methylbenzyl]-(RS)-proline methyl ester (16.3 g) was obtained in a yield of 77.8%.

$^1$HNMR (CDCl$_3$) δ 7.34–7.15 (m, 10H), 3.79–3.60 (m, 2H), 3.68 (s, 3H), 3.45 (s, 3H), 3.43–3.40 (m, 1H), 3.29 (dd, J=4.3 Hz, J'=3.9 Hz, 1H), 3.17–3.12 (m, 1H), 3.02–2.98 (m, 1H), 2.62–2.46 (m, 2H), 2.27–1.75 (m, 8H), 1.41 (d, J=3.6 Hz, 3H), 1.38 (d, J=3.9 Hz, 3H).

Example 2

L-tartaric acid (9.51 g) was mixed with methanol (14.18 g) and heated to 40° C. To the resulting solution was added dropwise a 50% toluene solution (28.93 g) of N-[(S)-α-methylbenzyl]-(RS)-proline methyl ester obtained in Example 1 at that temperature. After stirred at the temperature for 1 hour, the reaction mixture was cooled to 0° C. over 14 hours and stirred at that temperature for 2 hours. The crystallized solid was separated by filtration and washed with cold methanol to yield a salt of N-[(S)-α-methylbenzyl]-(S)-proline methyl ester and L-tartaric acid (11.50 g) in 98.8% diastereomeric excess (hereinafter referred to as "d.e.") and a yield of 40.0%.

$^1$HNMR (DMSO) δ 7.34–7.20 (m, 5H), 4.31 (s, 2H), 3.71 (q, J=6.6 Hz, 1H), 3.58 (s, 3H), 3.27 (dd, J=3.3 Hz, J'=8.7 Hz, 1H), 2.82 (q, J=6.7 Hz, 1H), 2.82 (q, J=8.0 Hz, 1H), 2.09–1.93 (m, 1H), 1.84–1.72 (m, 1H), 1.27 (d, J=6.6 Hz, 3H).

Example 3

The salt of N-[(S)-α-methylbenzyl]-(S)-proline methyl ester and L-tartaric acid obtained in Example 2 (7.67 g) was dissolved in water (15.57 g) at room temperature, and toluene (7.77 g) was added to the solution. To the mixture was added dropwise a 15.5% aqueous sodium carbonate solution (14.61 g), and the resulting mixture was stirred at that temperature for 1 hour. The organic layer was separated, and washed with water and condensed to yield N-[(S)-α-methylbenzyl]-(S)-proline methyl ester (4.46 g) in 99.2% d.e. and a yield of 95.6%.

$^1$HNMR (CDCl$_3$) δ 7.34–7.19 (m, 5H), 3.73 (q, J=6.9 Hz, 1H), 3.67 (s, 3H), 3.28 (dd, J=4.0 Hz, J'=8.9 Hz, 1H), 3.01–2.94 (m, 1H), 2.61–2.52 (m, 1H), 2.14–1.63 (m, 4H), 1.38 (d, J=6.9 Hz, 3H).

Example 4

To N-[(S)-α-methylbenzyl]-(S)-proline methyl ester (4.46 g) obtained in Example 3 were added water (9.33 g) and 2-ethylhexanoic acid (3.25 g). The mixture was heated up to 60° C. and stirred at that temperature for 12 hours. The resulting mixture was washed with heptane to yield an aqueous N-[(S)-α-methylbenzyl]-(S)-proline solution.

To the aqueous N-[(S)-α-methylbenzyl]-(S)-proline solution was added a 10% palladium hydroxide on carbon (0.70 g), and the mixture was heated up to 50° C. in an atmosphere of hydrogen and stirred at that temperature for 8 hours. After replacing the atmosphere with nitrogen, acetic acid (0.12 g) was added to the mixture which was then stirred at that temperature for 1 hour. After the catalyst were removed by filtration, the aqueous layer was separated. The aqueous layer was condensed to yield a crude crystal of (S)-proline (2.0 g) in a yield of 90%. The high-performance liquid chromatography analysis using an optically active column indicated 100% ee.

The crude crystals were dissolved in water (1.34 g) at 70° C., ethanol (18.78 g) was added dropwise to the solution. After the mixture was stirred at that temperature for 1 hour, it was cooled to 0° C. over 1.5 hours, and was stirred at that temperature for 1 hour. After that, crystals were separated by filtration and dried to yield (S)-proline (1.02 g) in a yield of 51%. The high-performance liquid chromatography analysis using an optically active column indicated 100% ee.

Example 5

Methyl N-[(S)-α-methylbenzyl]-(RS)-pipecolate (14.7 g) was prepared in a yield of 73.5% in the same manner as Example 1, except that methyl (RS)-2,5-dibromovalerate was replaced with methyl (RS)-2,6-dibromocaproate.

$^1$HNMR (CDCl$_3$) δ 7.41–7.16 (m, 10H), 3.98–3.86 (m, 2H), 3.72 (s, 3H), 3.71 (s, 3H), 3.78–3.66 (m, 2H), 3.14–3.02 (m, 2H), 2.74–2.67 (m, 1H), 2.35–2.33 (m, 1H), 2.15–1.53 (m, 12H), 1.43 (d, J=6.9 Hz, 3H), 1.26 (d, J=6.9 Hz, 3H).

Example 6

Methyl N-[(S)-α-methylbenzyl]-(RS)-pipecolate (157 mg) was dissolved in methyl tert-butyl ether (2 ml) at room temperature. To this solution was added a mixture of L-(+)-mandelic acid (86 mg) and methyl tert-butyl ether (2 ml) at room temperature and stirred. The resulting solution was allowed to stand at −20° C. for one day to form a crystal. The crystals were separated by filtration and dried to yield an L-(+)-mandelic acid salt of methyl N-[(S)-α-methylbenzyl]-(S)-pipecolate (79.9 mg) in an optical purity of 73% de and a yield of 23%.

Example 7

Methyl N-[(S)-α-methylbenzyl]-(RS)-pipecolate (159 mg) was dissolved in methyl tert-butyl ether (2 ml) at room temperature. To this solution was added a mixture of (2S)-L-(−)-malic acid (120 mg) and methyl tert-butyl ether (2 ml) at room temperature and stirred. The resultant solution was allowed to stand at −20° C. for one day to form crystals. The crystals were separated by filtration and dried to yield a (2S)-L-(−)-malic acid salt of methyl N-[(S)-α-methylbenzyl]-(S)-pipecolate (70.8 mg) in an optical purity of 41% de and a yield of 29%.

Example 8

L-(+)-mandelic acid (1.52 g) and toluene (8.67 g) were mixed and warmed to 70° C. To the solution was added a mixture of methyl N-[(S)-α-methylbenzyl]-(RS)-pipecolate (2.47 g) and toluene (8.67 g). The mixture was stirred for 0.5 hour, and the L-(+)-mandelic acid salt of methyl N-[(S)-α-methylbenzyl]-(S)-pipecolate, which was obtained in Example 6 (73% d.e.), as a seed crystal was added thereto. After this, the mixture was cooled to 0° C. over 3.5 hours with stirring. The crystals formed were separated by filtration and washed with cold toluene to yield an L-(+)-mandelic acid salt of methyl N-[(S)-α-methylbenzyl]-(S)-pipecolate (2.49 g) in 95.2% d.e. and a yield of 41.3%.

Example 9

An L-(+)-mandelic acid salt of methyl N-[(S)-α-methylbenzyl]-(S)-pipecolate (95% d.e.) prepared in the same manner as Example 8 (11.30 g), toluene (64.28 g) and methanol (2.40 g) were mixed and heated up to 70° C. To this solution was added the L-(+)-mandelic acid salt of methyl N-[(S)-α-methylbenzyl]-(S)-pipecolate, which was obtained in Example 8 (95.2% d.e.), as a seed crystal, and the mixture was cooled down to 0° C. over 3.5 hours with stirring. The crystals formed were separated by filtration and washed with cold toluene to yield an L-(+)-mandelic acid salt of methyl N-[(S)-α-methylbenzyl]-(S)-pipecolate (9.70 g) in an optical purity of 99.8% de and a yield of 85.8%.

$^1$HNMR (DMSO) δ 7.43–7.19 (m, 15H), 5.03 (s, 3H), 3.83 (q, J=6.6 Hz, 1H), 3.61 (s, 3H), 3.07–2.97 (m, 2H), 2.44–2.37 (m, 1H), 1.63–1.47 (m, 4H), 1.38–1.30 (m, 2H), 1.31 (d, J=6.6 Hz, 3H).

Example 10

Methyl N-[(S)-α-methylbenzyl]-(S)-pipecolate (5.86 g) was obtained in a yield of 100% in the same manner as Example 3, except that the salt of N-[(S)-α-methylbenzyl]-(S)-proline methyl ester and L-tartaric acid (7.67 g) was replaced with an L-(+)-mandelic acid salt of methyl N-[(S)-α-methylbenzyl]-(S)-pipecolate (13.79 g).

$^1$HNMR (CDCl$_3$) δ 7.38–7.20 (m, 5H), 3.98–3.90 (m, 1H), 3.75 (s, 3H), 3.18–3.06 (m, 2H), 2.43–2.35 (m, 1H), 1.92–1.22 (m, 6H), 1.47 (d, J=6.6 Hz, 3H).

Example 11

Methyl N-[(S)-α-methylbenzyl]-(S)-pipecolate (1.24 g) was dissolved in dioxane (27 g), and heated up to 50° C. To this solution was added dropwise a 1% aqueous sodium hydroxide solution (22 g), and the mixture was stirred at that temperature for 20 hours. The reaction mixture was condensed, and dioxane was added thereto. The precipitate was separated by filtration to yield a sodium salt of N-[(S)-α-methylbenzyl]-(S)-pipecolic acid (1.0 g) in a yield of 78%.

$^1$HNMR (D$_2$O) δ 7.53–7.46 (m, 5H), 4.88 (q, J=6.9 Hz, 1H), 3.8–3.6 (m, 1H), 3.3–3.2 (m, 1H), 2.7–2.5 (m, 1H), 2.2–2.1 (m, 1H), 1.9–1.7 (m, 1H), 1.76 (d, J=7.2 Hz, 3H), 1.3–1.1 (m, 1H).

Example 12

A sodium salt of N-[(S)-α-methylbenzyl]-(S)-pipecolic acid (0.93 g) was dissolved in water (6.1 g), and to the solution was added 10% palladium hydroxide on carbon (0.22 g). The mixture was heated up to 50° C. in an atmosphere of hydrogen, and stirred at that temperature for 6 hours. After replacing the atmosphere with nitrogen, to the mixture was added acetic acid (0.06 g), and stirred at that temperature for 1 hour. After this, the catalyst was removed by filtration, and the filtrate was separated into layers. The aqueous layer was condensed to yield sodium (S)-pipecolate (0.61 g) in a yield of 82%. The high-performance liquid chromatography analysis using an optically active column indicated 100% ee.

What is claimed is:

1. A process for producing the optically active cyclic amino acid ester derivative of the formula (I):

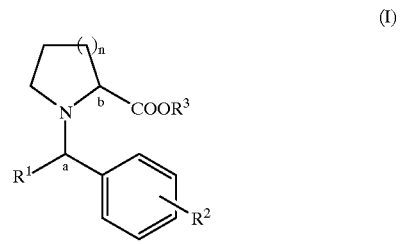

wherein R$^1$ represents a C1–C8 alkyl group;
R$^2$ represents a hydrogen atom, a C1–C8 alkyl group, a halogen atom, a hydroxy group or a C1–C8 alkoxy group;
R$^3$ represents an aryl group or a C1–C8 alkyl group, which alkyl group may be substituted with an aryl group;
"n" represents an integer from 1 to 4; and
"a" and "b" respectively represent R or S, which comprises the steps of:
(a) contacting a cyclic amino acid ester derivative of the formula (II):

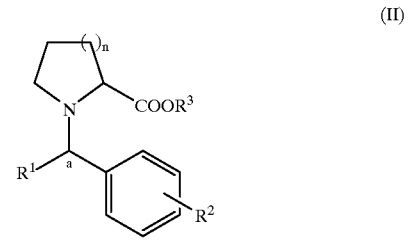

wherein R$^1$, R$^2$, R$^3$, "n" and "a" represent the same as defined above, with an optically active carboxylic acid of the formula (III):

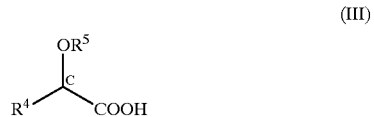

wherein R$^4$ represents:
a C1–C8 linear or branched alkyl group which may be substituted with at least one group selected from a phenyl group, a hydroxy group, a C1–C8 alkoxy group, a phenoxy group, an acyloxy group, a hydroxycarbonyl group, an alkoxycarbonyl group and a halogen atom;

a phenyl group which may be substituted with at least one group selected from a C1–C8 alkyl group, a phenyl group, a hydroxy group, a C1–C8 alkoxy group, a phenoxy group, an acyloxy group and a halogen atom; or a halogen atom, R⁵ represents:

a C1–C8 linear or branched alkyl group which may be substituted with at least one group selected from a phenyl group, a hydroxy group, a C1–C8 alkoxy group, a phenoxy group, an acyloxy group and a halogen atom;

a phenyl group which may be substituted with at least one group selected from a C1–C8 alkyl group, a phenyl group, a hydroxy group, a C1–C8 alkoxy group, a phenoxy group, an acyloxy group, a halogen atom and a nitro group;

an acyl group which may be substituted with at least one group selected from a C1–C8 alkyl group, a phenyl group, a hydroxy group, a C1–C8 alkoxy group, a phenoxy group, an acyloxy group, a halogen atom and a nitro group; or a hydrogen atom; and "c" represents: R or S;

(b) isolating a resulting salt comprising the compounds of the formulae (I) and (III); and (c) treating the isolated salt with an acid or a base.

2. The process according to claim 1, wherein the optically active carboxylic acid of the formula (III) is optically active mandelic acid, optically active malic acid, optically active tartaric acid or optically active O,O'-dibenzoyltartaric acid.

3. An essentially pure optically active cyclic amino acid ester derivative of the formula (I):

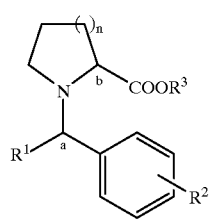

(I)

wherein R¹ represents a C1–C8 alkyl group;

R² represents a hydrogen atom, a C1–C8 alkyl group, a halogen atom, a hydroxyl group or a C1–C8 alkoxyl group;

R³ represents an aryl group or a C1–C8 alkyl group, which alkyl group may be substituted with an aryl group;

"n" represents an integer from 1 to 4; and

"a" and "b" are the same and represent an R or S configuration.

4. A salt comprising the optically active cyclic amino acid derivative of the formula (I) as defined in claim 1 and an optically active carboxylic acid of the formula (III) as defined in claim 1.

5. The salt according to claim 4, wherein the optically active carboxylic acid of the formula (III) is optically active mandelic acid, optically active malic acid, optically active tartaric acid or optically active O,O'-dibenzoyltartaric acid.

6. An optically active cyclic amino acid derivative of the formula (IV):

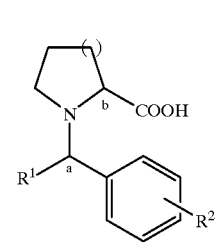

(IV)

wherein R¹, R², "n", "a" and "b" respectively have the same meaning as defined in claim 1.

7. A process for producing the optically active cyclic amino acid derivative of the formula (IV) as defined in claim 6, which comprises:

hydrolyzing the optically active cyclic amino acid ester derivative of the formula (I) as defined in claim 1 in the presence of an acid or a base.

8. A process for producing an optically active cyclic amino acid of the formula (V):

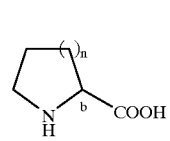

(V)

wherein "n" is an integer of 1 to 4, and "b" represents R or S, which comprises:

subjecting the optically active cyclic amino acid derivative of the formula (IV) as defined in claim 6 to a hydrogenolysis reaction in the presence of a catalyst.

9. The process according to claim 8, wherein the hydrogenolysis reaction is carried out with hydrogen, hydrazine or salts thereof, or formic acid or salts thereof.

10. The process according to claim 8, wherein the catalyst is palladium hydroxide on carbon, palladium carbon, palladium acetate, palladium chloride, palladium oxide or palladium hydroxide.

11. A cyclic amino acid ester derivative of the formula (II):

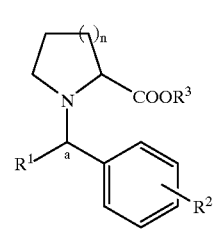

(II)

wherein R¹ represents a C1–C8 alkyl group;

R² represents a hydrogen atom, a C1–C8 alkyl group, a halogen atom, a hydroxyl group or a C1–C8 alkoxyl group;

R³ represents an aryl group or a C1–C8 alkyl group, which alkyl group may be substituted with an aryl group;

"n" represents an integer from 2 to 4; and a represents an asymmetric carbon atom having an R configuration.

12. A process for producing a cyclic amino acid ester derivative of the formula (II):

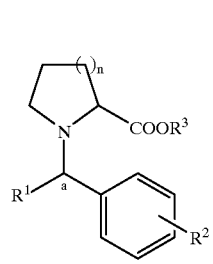
(II)

wherein $R^1$ represents a C1–C8 alkyl group:
$R^2$ represents a hydrogen atom, a C1–C8 alkyl group, a halogen atom, a hydroxyl group or a C1–C8 alkoxy group;
$R^3$ represents an aryl group or a C1–C8 alkyl group, which alkyl group may be substituted with an aryl group;
"n" represents an integer from 2 to 4; and
"a" represents an asymmetric carbon atom having an R or S configuration, which comprises:
reacting a di-substituted aliphatic carboxylic acid ester of the formula (VI):

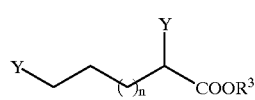
(VI)

wherein Y represents a leaving group,
$R^3$ and "n" have the same meaning defined above, with an optically active amine of the formula (VII):

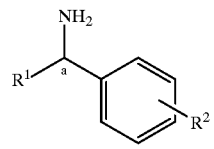
(VII)

wherein $R^1$, $R^2$ and "a" have the same meaning defined above.

13. The compound according to claim 3, wherein n is an integer of 2 to 4.

14. An essentially pure optically active cyclic amino acid ester derivative of the formula (I):

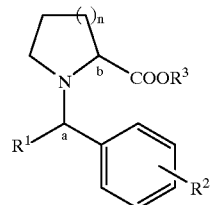
(I)

wherein $R^1$ represents a C1–C8 alkyl group;
$R^2$ represents a hydrogen atom, a C1–C8 alkyl group, a halogen atom, a hydroxyl group or a C1–C8 alkoxyl group;
$R^3$ represents an aryl group or a C1–C8 alkyl group, which alkyl group may be substituted with an aryl group;
"n" represents an integer of 1, 3 or 4; and
"a" and "b" independently represent an R or S configuration.

15. A cyclic amino acid ester derivative of the formula (II):

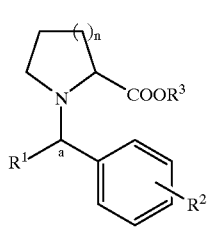
(II)

wherein $R^1$ represents a C1–C8 alkyl group;
$R^2$ represents a hydrogen atom, a C1–C8 alkyl group, a halogen atom, a hydroxyl group or a C1–C8 alkoxyl group;
$R^3$ represents an aryl group or a C2–C8 alkyl group, which alkyl group may be substituted with an aryl group;
"n" represents an integer from 2 to 4; and
"a" represents an asymmetric carbon atom having an R or S configuration.

16. An optically active cyclic amino acid ester derivative according to claim 3, wherein "a" and "b" represent an S configuration.

* * * * *